US007138146B2

(12) United States Patent
Miller et al.

(10) Patent No.: US 7,138,146 B2
(45) Date of Patent: Nov. 21, 2006

(54) ACROCHORDON ALLEVIATION

(76) Inventors: Mickey Miller, 4651 N. Alta Hacienda Dr., Phoenix, AZ (US) 85018; Margaret Ancira, 4651 N. Alta Hacienda Dr., Phoenix, AZ (US) 85018

(*) Notice: Subject to any disclaimer, the term of this patent is extended or adjusted under 35 U.S.C. 154(b) by 316 days.

(21) Appl. No.: 10/072,829

(22) Filed: Feb. 8, 2002

(65) Prior Publication Data

US 2003/0008018 A1 Jan. 9, 2003

Related U.S. Application Data

(60) Provisional application No. 60/267,978, filed on Feb. 9, 2001.

(51) Int. Cl.
*A61K 33/40* (2006.01)

(52) U.S. Cl. .................... 424/616; 514/251; 514/276; 514/356; 514/474

(58) Field of Classification Search ............... 424/616; 514/251, 276, 356, 474
See application file for complete search history.

(56) References Cited

U.S. PATENT DOCUMENTS

| 3,954,974 | A | 5/1976 | Herzog et al. ............... 424/130 |
| 4,018,802 | A | 4/1977 | Cragoe et al. ............... 260/399 |
| 4,128,564 | A | 12/1978 | Cragoe et al. ............... 260/401 |
| 4,438,102 | A | 3/1984 | Ganci ........................ 424/130 |
| 4,485,091 | A | 11/1984 | Fitton ........................ 424/62 |
| 4,826,681 | A | 5/1989 | Jacquet et al. ............... 424/613 |
| 5,362,915 | A | 11/1994 | Maschler et al. ............ 568/20 |
| 5,380,764 | A | 1/1995 | Herzog ....................... 514/859 |
| 5,472,715 | A | 12/1995 | Uehara ....................... 424/613 |
| 5,594,015 | A | 1/1997 | Kurtz et al. .................. 514/369 |
| 5,736,582 | A | 4/1998 | Devillez ...................... 514/859 |
| 5,824,694 | A | 10/1998 | Kurtz et al. .................. 514/369 |
| 5,958,984 | A | 9/1999 | Devillez ...................... 514/714 |
| 6,028,104 | A | 2/2000 | Schmidt et al. ............. 514/557 |
| 6,146,640 | A | 11/2000 | Kyke .......................... 424/195.1 |

FOREIGN PATENT DOCUMENTS

GB 2285218 7/1995

OTHER PUBLICATIONS

Beitler et al., "Association between acrochordons and colonic polyps," *J. Am. Acad. Dermatol.*, 14:1042–1044, 1986.

Bilotta and Waye, "Hydrogen Peroxide Enteritis: the "Snow White" Sign," *Gastrointestinal Endoscopy*, 35: 428–430; 1989.

Christensen et al., "Fatal Oxygen Embolization after Hydrogen Peroxide Ingestion," *Critical Care Medicine*, 20(4): 543–544; 1992.

Cornell and Stoughton, "Correlation of the vasoconstriction assay and clinical activity in Psoriasis," *Arch Dermatol.*, 121:63–67, 1985.

Danis Brodeur, "The Danger of Hydrogen Peroxide as a Colonic Irrigating Solution," *Journal of Pediatric Surgery*, 2(2): 131–133; 1967.

Dickson et al., "Hydrogen peroxide exposure—325 exposures reported to a regional poison control center," *Clinical Toxicology*, 32(6):705–714, 1994.

Ellis et al., "Increased epidermal growth factor receptors in seborrheic keratoses and acrochordons of patients with the dysplastic nevus syndrome," *J. Am. Acad. Dermatol*, 23:1070–1077, 1990.

Giberson et al., "Near–fatal hydrogen peroxide ingestion," *Annals of Emergency Medicine*, 18:119–120/778–779, 1989.

Goette et al., "Skin Blanching Induced by Hydrogen Peroxide," *Southern Medical Journal*, 70(5): 620–622; 1977.

Goette, "Hydrogen peroxide–induced skin blanching," *Arch Dermatol*, 112:1788–1789, 1976.

Gruber et al., "The effect of commonly used antiseptics on wound healing," *Antiseptics and Wound Healing*, 55(4):472–476, 1975.

Henry et al., "Hydrogen Peroxide 3% Exposures," *Clinical Toxicology*, 34(3): 323–327; 1996.

Hocutt, "Skin cryosurgery for the family physician," *American Family Physicians*, 48:445–452, 1993.

Humberston et al., "Ingestion of 35% Hydrogen Peroxide," *Clinical Toxicology*, 28(1):95–100; 1990.

Klein–Szanto and Slaga, "Effects of Peroxides on Rodent Skin: Epidermal Hyperplasia and Tumor Promotion," *The Journal of Investigative Dermatology*, 79: 30–34; 1982.

Leavitt et al., "Skin tags: a cutaneous marker for colonic polyps," *Annals of Internal Med.*, 98:928–930, 1983.

Nanney et al., "Altered distribution of phospholipase C–γ1 in Benign hyperproliferative epidermal diseases," *Cell Growth & Differentiation*, 3:233–239, 1992.

Nanney et al., "Epidermal growth factor receptors in idiopathic and virally induced skin diseases," *Am. J. Pathology*, 140(4):915.

O'Toole et al., "Hydrogen Peroxide Inhibits Human Keratinocyte Migration," *Dermatologic Surgery*, 22: 525–529; 1996.

Oliver and Murphy, "Influenzal Pneumonia: the intavenous injection of hydrogen peroxide," *The Lancet*, 432–433, 1920.

(Continued)

*Primary Examiner*—Leon Lankford
(74) *Attorney, Agent, or Firm*—Rosenbaum & Associates, PC; Stinson Morrison Hecker LLP

(57) ABSTRACT

The subject of the present invention is acrochordon removal and prevention utilizing safe dependable effective biocompatable treatments with no scarring, bleeding, twisting, yanking, choking, burning, freezing, shocking, screaming and hypo pigmentation or hyper pigmentation. In one aspect of the invention, methods are provided for acrochordon removal comprising application of high concentrations of hydrogen peroxide.

71 Claims, No Drawings

OTHER PUBLICATIONS

Pumphrey, "Hydrogen peroxide procitits," *American J. of Surgery,* 81:60–62, 1951.

Rathbun, "A Method for Removing the Acrochordon (Skin Tag)," *Kansas Medicine,* 91(1): 11–12; 1990.

Sebben, "The hazards of electrosurgery," *J. Am. Acad. Dermatol.,* 16(4):869–872, 1987.

Segal, "Liquid nitrogen therapy," *Australian Family Physician,* 13:356–357, 1984.

Strohmer et al., "Use of hydrogen peroxide for vaginal contraception," *Human Reproduction,* 12:1599, 1997.

Strother, "Acrochordonectomy made easy," *Clinician Reviews,* 8(3):154–155, 1998.

Tegner and Björnberg, "Hydrogen Peroxide Cream for the Prevention of White Pressure Areas in UVA Sunbeds," *Acta Dermatologica Venereologica (Stockholm),* 70: 75–76; 1990.

Tegner, "Induction of Skin Blanching by Hydrogen Peroxide," *Acta Dermatologica Venereologica (Stockholm),* 74: 474–475; 1994.

Tur et al., "Topical hydrogen peroxide treatment of ischemic ulcers in the guinea pig: blood recruitment in multiple skin sites," *Journal of the American Academy of Dermatology,* 33: 217–221; 1995.

"Seborrheic and Senile Keratoses" by M.R. Caro, et al., *Medical Clinics of North America,*vol. 35, pp. 419–431.

"Differenting Seborrheic Keratosis from Skin Neoplasm" by R.W. Cashmore, et al., *Geniatrics,*vol. 40, pp. 69–75 (1985).

"Curetting for Seborrheic Keratose" by J.L. Eberlin, *Plastic and Reconstructive Surgery,*vol. 101, No. 2, pp. 546–547 (1998).

"Malignant Melanoma Appearing in a Seborrhoeic Keratosis" by M. Jones–Caballero, et al., *British Journal of Dermatology,*vol. 133, pp. 1016–1018 (1995).

"Cellular Response of Seborrheic Keratosis Following Croton Oil Irritation and Surgical Trauma with Special Reference to Melanoacanthoma" by B. Mevorah, et al., *Dermatologica,* vol. 131, pp. 452–464 (1965).

"Seborrhoeic Keratoses: Scarless Removal by Curettage and Oxidized Cellulose" by F.E. Mohs, *Journal of the American Medical Association,* vol. 212, No. 11, pp. 1956–1958 (1970).

"The Management of Seborrhoeic Keratoses by General Practitioners, Surgeons, and Dermatologists" by J.M. Sowden, et al., *British Journal of Dermatology,* vol. 139, pp. 348–349 (1998).

"Cryosurgery for Common Skin Lesions: Treatment in Family Physicians' Offices" by S.J. Wetmore, *Cutis,*vol. 63, pp. 235–237 (1999).

"Malignant Melanoma Appearing in Seborrheic Keratosis" by J.B. Yakar, et al., *Journal of Dermatologic Surgery and Oncology,* vol. 10, pp. 382–383 (1994).

Lee and Choi, "TCA chemical peeling. Procedures, complication and self–evaluation of therapeutic effect in 242 patients," *Korean Journal of Dermatology,*31:1–8, 1993, (ABSTRACT).

CV2003–020242, Physicians Choice of Arizona, Inc. vs. Mickey Miller et al., Mickey Miller's Answer and Counter Claim, filed Dec. 2, 2003.

ACROCHORDON ALLEVIATION

BACKGROUND OF THE INVENTION

This application claims the priority of U.S. Provisional Patent Application Ser. No. 60/267,978, filed Feb. 9, 2001.

FIELD OF THE INVENTION

The present invention concerns safe, effective topical compositions for the removal and prevention of acrochordons.

DESCRIPTION OF RELATED ART

Acrochordon carriers have suffered for thousands of years, due to the lack of a safe, convenient treatment for the removal and prevention of acrochordons. Medical practitioners since ancient times have searched for a solution to the acrochordon problem. Nevertheless, even today practitioners typically advise no treatment unless a specific acrochordon causes a problem, for example, due to pedicle strangulation. A survey of the medical literature back to 450B.C. produces no evidence of advice a medical practitioner has given for the prevention of acrochordons.

The word acrochordon does not appear in the patent files of the United States of America. It is believed that prior methods for acrochordon removal and prevention are lacking because the methods so far employed have produced such unsatisfactory results. Prior methods of acrochordon removal produced bleeding, scarring, infection, pain, long recovery time, contamination, hypo pigmentation and hyper pigmentation. Previously known methods of acrochordon removal by medical practitioners include twisting, clamping, pulling, yanking, choking, burning, freezing, shocking, cutting and microwaving. Several methods of acrochordon removal currently in use by medical practitioners pose a significant risk of hepatitis B, human papillomavirus and human immunodeficiency virus contamination to patients and medical personnel alike.

The Greek physician Hippocrates, c.460–c.370 B.C., recognized as the father of medicine, originated the name akrochordon meaning "like a chord" to the nasty, detestable, repugnant, disfiguring pedunculated excrescences of cutaneous tissue his pleading patients found sprouting from their integument. The best efforts of Hippocrates over a period of many years did not result in a safe, convenient, dependable treatment for the removal and prevention of acrochordons. Hippocrates, in all probability, finally realized it superior to defer treatment of acrochordons in order to avoid patient dissatisfaction or to increase the cost of acrochordon removal in order to accommodate only the most insistent acrochordon removal requests, as is done by current medical practitioners.

Aulus Cornelius Celsus, c.A.D.3–c.A.D.6, considered the greatest Roman medical writer, who recommended cleanliness and the washing of wounds with antiseptic substances such as vinegar, spoke of acrochordons as tumors resembling warts. According to Celsus, "one kind the Greeks called akrochordon, wherein is a development of something hard and uneven under the skin, the latter retaining its natural color". The methods of acrochordon removal employed by Aulus Cornelius Celsus were for the most part probably similar to the methods originated by the father of medicine, Hippocrates.

Paulus AEgineta, 700A.D., referred to the cellular tissue polypi known as acrochordons thusly: "The akrochordon is a small rising of the surface, free of pain, callous, for the most part round and heavy, a narrow base so as to appear to hang. It is so called from its resemblance to the end of a cord." No doubt acrochordon removal techniques utilized in the time of Paulus AEgineta were not dissimilar to the acrochordon removal methods employed by the great medical men such as Hippocrates, Galen, Celsus, Dioskurides and Orebiasis.

The nosology of acrochordons is replete with controversies in both classification and description of the pedunculated excrescences of cutaneous tissue known as acrochordons. The ninth class of Plenck's classification published in 1777 includes excrescentiae cutaneae, and under this head warts are included, of which he makes nine varieties, the second of which are pendulous warts (hägende, warze, stengelwarze), which include acrochordons, which he says hang from the skin by means of a little stem.

Erasmus Wilson, a prominent nineteenth century dermatologist, in his chapter on developmental and nutritive affections in the seventh edition of his authoritative dermatology book entitled *Diseases of the Skin* published in Philadelphia in 1868, considers these pendulous growths of the skin under the term "ecphyma" and allied to warts. Dr. Wilson classifies ecphyma under two varieties: ecphyma mollusciforme and ecphyma acrochordon.

The first variety, ecphyma mollusciforme, is a prominence of the skin produced by simple growths of the integument, more or less pedunculated, sometimes sessile, of sizes between a pea and a walnut. Conventional removal methods of this type of soft fibroma do not differ to any appreciable degree from the conventional methods employed for acrochordons. Compositions of the present invention may be specially formulated to provide for the satisfactory elimination of this type of cutaneous lesion.

The second variety, ecphyma acrochordon, that Dr. Wilson felt were a diminutive form of ecphyma mollusciforme, are by far the most common and are the main subject matter of the present invention.

In 1905, Dr. Samuel M. Brickner described a new clinical entity, "Fibroma Molluscum Gravidarum", in a presentation to the obstetrical section of the New York Academy of Medicine.

Acrochordon nosochthonography indicates a total global affliction situation with perhaps higher acrochordon concentrations in the colder climates where acrochordon afflictees practice high occlusion and heavy carbohydrate consumption combined with Nordic ancestry.

At the Institute of Dermatological Clinic and the Department of Cellular & Developmental Biology in the 'La Sapienza' University of Rome, human papillomavirus DNA has been detected in acrochordons by using polymerase chain reaction assays. Human papillomavirus is an epitheliotropic virus associated with benign cutaneous and mucosal lesions (cutaneous warts, genital condylomas and laryngeal papillomas) and less frequently with malignant tumours.

The finding that HPV 6/11 is present in a high percentage of biopsies from acrochordons suggests that this virus may be involved in the pathogenesis of these cutaneous lesions. No significant correlation was found between the presence of HPV DNA in acrochordons and their localization, sex or age of patients; they shared only a significant overweight condition. In the view of doctors C. Dianzini, S. Calvieri, A. Pierangeli, M. Imperi, M. Bucci and A. M. Degener, working under a partly supported grant from Institut Pasteur/Fondazione Cenci Bolognetti, the clinical behaviour of acrochordons is such that they spread locally in the same subject but rarely to other individuals. The low quantity of HPV DNA present in acrochordons may be explained by mutations or deletions of the HPV genome and may also correlate with the clinical evolution of these lesions. While the presence of HPV sequences in acrochordons cannot be considered as proof of an aetiological role, the expression of early viral genes may contribute to the deregulation of cell cycling. In the presence of HPV DNA, the degree of cellular differentiation and mechanical friction seem to be significant cofactors in the pathogenesis of acrochordons. The almost constant association between HPV DNA and acrochordons indeed suggest a role for HPV in the pathogenesis of these cutaneous lesions. The demise of the HPV in acrochordons by treatment with the present invention may explain why so few reoccur after treatment with the present invention for acrochordon removal and prevention.

Electrocautery, not unlike the red-hot iron torture much in favor during the Middle Ages, is noted for the high smoke output and pungent odor of burning acrochordons. Often times when other patients in the waiting room get a waft of the odor resulting from the use of the electrocautery device in use they reconsider treatment.

High-frequency electrosurgery has provided dermatology and other areas of medicine with an efficient means of tissue destruction and hemostatis. When electrosurgery is used for simple office procedures, little attention is given to risks of contamination. Indirect contamination can occur as a result of the aerosolization of blood droplets secondary to mechanical actions at the high-frequency electrosurgery site. Hepatitis B or human immunodeficiency disease might be spread through aerosolized microdroplets of blood and electrosurgical smoke. Every medical practitioner and dermatologist who practices high-frequency electrosurgery should thus provide surgical masks and eye protection to everyone in the premises and sterilize all exposed surfaces.

Electrocoagulation incorporates the patient into the electrical circuit with the use of a dispersive electrode plate. This dispersive electrode plate allows the machine to deliver a larger amount of current to the patient. Electrocoagulation occurs when electrosugical current is applied to the tissue with resistance (ohmic) heat production that cooks tissue. The cooked tissue produces aerosolized microdroplets of blood and electrosurgical smoke. The mechanical action of electrosurgical current entering tissue can give rise to very small blood droplets that can travel a great distance. These droplets get scattered all about the surgical field. Of further concern is the problem of the microdroplets that cannot be seen but may be inhaled or received through the conjunctival surfaces.

Electrodesiccation is the superficial dehydration of tissue as a result of the passage of high-frequency current. Acrochordon removal with electrodsiccation has not proven to be very successful.

The smoke generated by laser surgery is capable of carrying viable viral particles. Acrochordon elimination attempts with various lasers commonly used in dermatology such as the carbon dioxide, erbium:YAG, and ND:YAG have been so disappointing that not one article has appeared regarding the success of lasers with acrochordon elimination in a controlled clinical study.

Cryosurgery of acrochordons with liquid nitrogen and carbon dioxide has been found to cause dischromic patches due to freezing of the skin surrounding the base of the pedicle. Monfrecola et al. propose a solution to the dischromic patch problem produced by cyrosurgery of acrochordons whereby the acrochordon is once again crushed with a clamp and this time the clamp is frozen instead of left hanging for fifteen minutes. The crushed and frozen acrochordon swells up after four days and then dies after 7 to 10 days. Recovery of the patient takes up to three weeks versus short recovery time using the present invention.

The most recent acrochordon removal method described in a medical journal is by Germaine D. Strother. In the on-line journal *Clinician Reviews®*, Doctor Strother details a procedure whereby a surgical clamp is used to crush the base of the acrochordon for fifteen minutes. The clamp is then removed and the acrochordon is cut off with scissors and a bandage applied. Doctor Strother does not say what she does when the patient has multiple acrochordons as is almost always the case. If a patient has, for example, more than thirty acrochordons, then Dr. Strother's procedure would take eight hours, not including time for cleaning and preparing the lesion and surrounding area or post treatment bandaging. If, on the other hand, Doctor Strother uses more than thirty surgical clamps, one at the base of each acrochordon, patient tolerance is assuredly lost. It is procedures such as the Strother acrochodonectomy that emphasize the need for the present invention for acrochordon removal and prevention.

Acrochordons are the fifth leading cause of visits to dermatologists, according to Henry H. Roenigk, Jr. M. D., a leading dermatologists with the Mayo Clinic in Scottsdale, Ariz. Since the start of his practice in dermatology, Dr. Roenigk has had no suitable acrochordon treatment for his patients. These patients often times also have carbohydrate intolerance, obesity, diabetes mellitus, colonic polyps, acromegaly, Birt-Hogg-Dube syndrome, human papillomavirus infection, polycystic ovarian disease and/or depression which are all correlated with acrochordons.

In 1987, Banik and Lubach discovered that 46% of the people checked had acrochordons. Banik and Lubach also state the relevant dermatological literature does not contain any details on the frequency of skin tags with regard to age and sex, but we may surmise millions of people to be suffering worldwide. The high percentage of persons with acrochordons emphasizes the need for the present invention for acrochordon alleviation.

Twenty-five dermatologists and medical doctors in metropolitan practice were surveyed as to acrochordon removal method, side effects, pricing, insurance reimbursement, and appointment lead-time. Fifty-two percent of the dermatologists surveyed used the inject, cut, burn, bandage method of acrochordon removal with no form of acrochordon prevention. Forty-eight percent of the dermatologists and medical doctors surveyed used the freeze, cut, thaw and bandage technique. All of the dermatologists and medical doctors surveyed reported scarring after their particular type of treatment. None of the dermatologists or medical doctors surveyed reported using any type of topical treatment, clearly pointing to the need for the present invention for acrochordon alleviation.

SUMMARY OF THE INVENTION

The present invention overcomes these and other drawbacks in the art by providing improved treatments for the alleviation of acrochordons. More particularly, it is a goal to provide a safe, effective means of removing even large numbers of acrochordons anywhere on the carrier.

There is provided, according to the present invention various embodiments of products designed for the acrochordon afflicted person to apply at home to remove unwanted acrochordons. Acrochordon type and location determine which specific acrochordon product and method is to be employed.

Reactive oxygen species such as the superoxide anion, hydrogen peroxide and hydroxyl radicals are utilized to remove acrochordons. In particular, hydrogen peroxide in a concentration far above levels encountered in mammalian metabolism is applied until the offending acrochordon is eliminated from the skin.

In one aspect of the invention, a method is provided for the removal of acrochordons comprising: (a) obtaining a composition comprising hydrogen peroxide in a concentration of at least 23 percent; (b) and applying said composition to an acrochordon on an acrochordon afflicted person or domesticated animal. In certain embodiments of the invention, a concentration of hydrogen peroxide used may be least 23, 27, 30, 35, 40 43 or at least 48 percent and may also be from about 23 percent to about 60 percent; from about 35 percent to about 60 percent; from about 35 percent to about 40 percent, from about 40 percent to about 50 percent and from about 43 percent to about 48 percent.

In another aspect of the invention, a composition used in accordance with the methods of the invention may comprise ingredients in addition to hydrogen peroxide, for example, at least one vitamin. In one embodiment of the invention, the vitamin is selected from the group consisting of ascorbic acid, niacin, thiamin and riboflavin and may also be L-ascorbic acid. The composition may also comprise at least one amino acid, including, for example, tyrosine, phenylalanine, carnitine, arginine, glycine, alanine, valine, leucine, isoleucine, serine, threonine, cysteine, cystine, methionine, asparagine, glutamine, lysine, 5-hydroxylysine, histidine, tryptophan, proline, ornithine, and carnosine. In one embodiment of the invention, the amino acid is L-carnitine.

In another aspect of the invention, a composition used in accordance with the methods of the invention may comprise at least one melanin inhibitor. Examples of such melanin inhibitors include hydroquinone, niacinimide, cinnamic acid, gamma-L-glutamyl-L-cystine, gamma-L-cysteine, oxidized glutathione, phenol, polyphenol, linoleic acid, ellagic acid, glycyrrhizic acid, alkylsalicylic acid, kojic acid, kojic acid glycosides, kojic acid succinimide ester, kojic acid dimer, thiazoles, propionic acid, sulphur, kudzu root, lavanol, caffeic acid, dicaffeoylquinic acid, tricaffeoylquinic acid, vitamin K, hydantoin, tranexamic acid, chromone derivative, indomethicin methacin, erthorbic acid, glucoside, conchiolin hydrolyzate, licorice root extract, logwood extract, gromwell seed extract, arbutin, chitosan, superoxide dismutase, melanostatin, S-lactoyl glutathione, and hydroquinone glycoside. In one embodiment of the invention the melanin inhibitor is kojic acid.

In still yet another aspect of the invention, a composition used in accordance with the methods of the invention may comprise at least one organic acid. Examples of such an organic acid include lactic acid, citric acid, isocitric acid, glycolic acid, malic acid, tartronic acid, tartaric acid, glucoronic acid, pyruvic acid, acetyl pyruvic acid, β-fluoropyruvic acid, 2-hydroxy isobutyric acid, galacturonic acid, salicylic acid, succinic acid, mandelic acid, β-phenyllactic acid, saccharic acid, β-phenylpyruvic acid, α-hydroxybutyric acid, α-hydroxyisobutyric acid, mucic acid, atrolactic acid, glucoheptonic acid, gluconic acid, glyceric acid, quinic acid, glyceruric acid, threuric acid, erythreuric acid, xyluric acid, lyxuric acid, arabinuric acid, riburic acid, iduric acid, guluric acid, mannuric acid, altruric acid, alluric acid, taluric acid, xylaric acid, lyxaric acid, trihydroxybutanoic acid, pentahydroxyhexanoic acid, and hexahydroxyheptanoic acid. In one embodiment of the invention, the organic acid is L-lactic acid.

In still yet another aspect of the invention, a composition used in accordance with the methods of the invention may comprise at least one hormone. Examples of such hormones include dehydroepiandrosterone, progesterone, estrogen, melatonin, testosterone, pregnenolone, thyroid hormone, thymus hormone, human growth hormone and melatonin. A composition used with the invention may also comprise at least one sulfoxide. Examples of such a sulfoxide include is selected from the group consisting of dimethylsulfoxide and decylmethylsulfoxide. In one embodiment of the invention, the sulfoxide is dimethylsulfoxide.

In still yet another aspect of the invention, a composition used in accordance with the methods of the invention may comprise at least one alcohol, including ethanol, propanol, butanol, pentanol, hexanol, octanol, nonanol, decanol, 2-butanol, 2-pentanol, benzyl alcohol and ethanol. The composition may also comprise at least one fatty acid, including valeric acid, heptanoic acid, pelagonic acid, caproic acid, capric acid, lauric acid, myristic acid, stearic acid, oleic acid, caprylic acid and myristic acid. The composition may still further comprise at least one fatty acid ester, including isopropyl myristate, isopropyl palmitate, octyldodecyl myristate, ethyl acetate, butyl acetate, methyl acetate, methylvalerate, methylpropionate, diethyl sebacate, ethyl oleate and isopropyl palmitate. The composition may also comprise at least one polyol, including propylene glycol, polyethylene glycol, ethylene glycol, diethylene glycol, triethylene glycol, dipropylene glycol, glycerol and propylene glycol. The composition may also comprise at least one amide, icnluding urea, dimethylacetamide, diethyltoluamide, dimethylformamide, dimethyloctamide, dimethyldecamide, hexamethylenelauramide, diethanolamine, triethanolamine and dimethylformamide.

In still yet another aspect of the invention, a composition used in accordance with the invention may be applied with a brush, dropper, atomizer, injector, sprayer, or pipette.

In still yet another aspect of the invention, a composition used in accordance with the invention may comprises at least one surfactant, including sodium laurate, sodium lauryl sulphate, cetyltrimethyl ammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride, Poloxamer (231, 182, 184), Brij (30, 93, 96,99), Span (20, 40, 60, 80), Myrj (45, 51, 52), Miglyol 840, sodium cholate, sodium salts of taurocholic, glycholic, desoxycholic acids and lecithin. A composition used may also comprise at least one terpene, including D-limonene, α-pinene, β-carene, α-terpineol, terpinen-4-ol, carvol, carvone, pulegone, piperitone, menthone, cyclohexene oxide, limonene oxide, α-pinene oxide, cyclopentene oxide, 1,8-cineole, ylang ylang, anise, chenopodium and eucalyptus. The composition may also comprise at least one alkanone, including N-heptane, N-octane, N-nonane, N-decane, N-undecane, N-dodecane, N-tridecane, N-tetradecane, and N-hexadecane. The composition may still further comprise aloe vera. In still yet another aspect of the invention, a composition used in accordance with the invention may comprise at least one gamma linolenic precursor, including borage oil, black currant oil, and evening primrose oil.

In still yet another aspect, the invention provides a method for the removal of acrochordons comprising: (a) obtaining a composition comprising hydrogen peroxide in a concentration of at least 23 percent and at least one compound selected from the group consisting of a vitamin, an amino acid, a melanin inhibitor, an organic acid, a hormone, a sulfoxide, an alcohol, a fatty acid, a fatty acid ester, a polyol, an amide, a surfactant, a terpene, an alkanone, aloe vera, and a gamma linolenic precursor; and (b) applying said composition to an acrochordon on an acrochordon afflicted person or domesticated animal. In certain embodiments of the invention, the concentration of hydrogen peroxide is at least 23, 27, 30, 35, 40, 43 or 50%, including from about 23 percent to about 60 percent, from about 35 percent to about 60 percent, from about 35 percent to about 40 percent, from about 40 percent to about 50 percent, and from about 43 percent to about 48 percent. In one embodiment, the composition may additionally comprise kojic acid, dimethylsulfoxide, melatonin, L-ascobic acid and ethanol; including about 26 percent hydrogen peroxide, 2 percent kojic acid, 12 percent dimethylsulfoxide, 0.5 percent melatonin, 1 percent L-ascobic acid and 15 percent ethanol. In another embodiment of the invention, the composition may additionally comprise lactic acid, niacin, testosterone, licorice root extract, and β-phenylpyruvic acid; including a composition of 47 percent hydrogen peroxide, 14 percent lactic acid, 2 percent niacin, 2 percent testosterone, 1 percent licorice root extract, and 0.5 percent β-phenylpyruvic acid. In yet another embodiment of the invention, the composition may additionally comprise L-tyrosine, phenylalanine, tricaffeoylquinic acid and ethanol; including a composition of 23 percent hydrogen peroxide, 2 percent L-tyrosine, 2 percent phenylalanine, 1 percent tricaffeoylquinic acid, and 18 percent ethanol.

In the method, the composition may also additionally comprise lactic acid, glycolic acid, salicylic acid, citric acid, and ethanol; including a composition of about 23 percent hydrogen peroxide, 4 percent lactic acid, 4 percent glycolic acid, 4 percent salicylic acid, 4 percent citric acid, and 20 percent ethanol. The composition may also comprise dimethysulfoxide; including a composition of about 35 percent hydrogen peroxide and 35 percent dimethysulfoxide. The composition may still further comprise L-ascorbic acid, niacin, glycine, hydroquinone, superoxide dismutase, galacturonic acid and ethanol; including a composition of about 35 percent hydrogen peroxide, 0.5 percent L-ascorbic acid, 0.5 percent niacin, 0.5 percent glycine, 0.5 percent hydroquinone, 0.5 percent superoxide dismutase, 5 percent galacturonic acid and 14 percent ethanol. In another embodiment of the invention, the composition may additionally comprise decylmethylsulfoxide; including a composition of 60 percent hydrogen peroxide and 6 percent decylmethylsulfoxide.

DETAILED DESCRIPTION OF THE INVENTION

The present invention provides an effective method for removal and treatment of unsightly acrochordons while avoiding the pain and scarring that accompanies presently known techniques. The inventors have discovered that providing one or more applications of a composition including hydrogen peroxide with a concentration of at least 23 percent results, surprisingly, in the complete removal of acrochordons, and other unsightly or undesirable skin disorders, without causing scarring. The method of the invention involves a precise topical application of the composition directly to the selected acrochordon. The composition may be left on the treated acrochordon without removal or further treatment after each application.

Preferred compositions and methods of acrochordon removal and prevention exhibit a high degree of efficacy in accomplishing successful removal and prevention of acrochordons anywhere on the skin including eyelids, groin and axillae. Acrochordon removal and prevention treatments of the present invention may include components with a high degree of bio-compatibility, such as products of mammalian metabolism, components of the electron transport chain and may include hydrogen peroxide, amino acids, vitamins, organic and/or inorganic minerals; alpha hydroxy, beta hydroxy, carboxylic or keto acids, hormones, enzymes, coenzymes and various penetration enhancers. Other components such as botanical actives and/or organic oxides and reductants may also be employed, as is known to those of skill in the art. Such compounds may be contained in a solvent such as water or another solvent compatible with hydrogen peroxide. Further, physiologically acceptable adjuvants may also be chosen, for example, pH-regulating agents, antioxidants, preservatives, pigments and colourings, emollients, antifoams, plant or animal oils or waxes, silicones, perfumes, surfactants, plasticizers, thickening polymers other compounds. Of course, persons skilled in the art will be careful to choose any such optional additional compounds and their quantity so that the active properties of the hydrogen peroxide are not substantially reduced by the addition.

Some patients may experience a burning or stinging sensation upon the application of the composition, particularly when higher concentrations of hydrogen peroxide are used. While the composition may be left on without further treatment even when a burning or stinging sensation occurs, it may be desirable to further treat the affected area with a neutralizing composition, such as water or a lotion or cream.

For total depedunculation of the acrochordon to occur, more than one application of the composition to the acrochordon will typically be necessary. It is envisioned that some smaller, narrow base type 1 acrochordons may be removed upon one application with a composition including hydrogen peroxide at higher concentrations, such as about 38 to 55 percent. However, total removal of the acrochordons, which may be treated with the present method will generally require several applications of the compositions described herein over a period of time. The applications may be spaced minutes or hours or days apart. It is preferred that subsequent treatments occur within two or three days of the previous treatment, although they may be as much as a week or two apart. The spacing of the treatments will depend upon such factors as patient sensitivity and type or types of the acrochordons present on the acrochordon afflicted individual.

While described in terms of acrochordon removal, the present invention is also effective in removing other skin conditions. These conditions include corns, warts, actinic keratoses, seborrheic keratoses, herpes, acne, rosacea, basil cell carcinoma, squamous cell carcinoma, onychomycosis, hyperpigmentation, rhytides, psoriasis and melanoma.

While the method of the invention is surprisingly and unexpectedly effective using a composition including simply hydrogen peroxide at concentrations above about 23 percent, including at least about 27, 30, 35, 40, 43 or 48 percent. As used herein, "percent" means percent by weight (w/w). The compositions for use in the present methods may also include other substances to aid in penetration, to enhance skin lightening, to aid in moisturizing or conditioning the skin, as will be known to those of skill in the art in view of the instant disclosure. For example, other ingredients may be added to improve the skin condition or the effectiveness of the compositions. Vitamins may added to the compositions to aid in improving the skin condition thereby inhibiting the production of subsequent cutaneous anomalies after treatment of the original condition.

Case histories of patients who have had various types of lesions successfully removed using the methods of the invention are provided below. These case histories and the examples that follow are included for illustrative purposes only and are not meant to limit the scope of the invention in any way.

CASE HISTORIES

Case History Number 1

A female acrochordon carrier with possible prolonged symptoms of fibroma molluscum gravidarum or fibroma molluscum gravidarium due to a multiplicity of contributing factors presented at the acrochordon treatment center with sixty three acrochordons. An acrochordon history was completed by the acrochordon carrier and an acrochordon examination was conducted with acrochordon positive confirmation and discovery of a high acrochordon concentration about the front and sides of neck. Acrochordon digital documentation was profusely performed, after which treatment possibilities utilizing treatments described in the present invention were offered to the acrochordonette and accepted with positive enthusiasm.

A conservative treatment approach was employed due to the skin sensitivity factor and the hereditary makeup of the acrochordon afflicted despondent. A multi-step biocompatible depedunculation treatment protocol was performed utilizing 45 percent hydrogen peroxide and the acrochordoniac was provided with appropriate acrochordon home products and an acrochordon prevention regimen was outlined. Subject returned for a second weekly acrochordon treatment session reporting great satisfaction with the high percentage of acrochordon depedunculation. Third weekly acrochordon treatment session same as second acrochordon treatment session with further acrochordon depedunculation. Fourth weekly acrochordon treatment session revealed remaining acrochordons, which were the most robust at acrochordon treatment initiation, to have lost their external layer and exhibit a pink core that was treated with a gentle removal protocol. Further profuse digital documentation was performed. Fifth and final acrochordon removal treatment session resulted in complete successful elimination of all acrochordons with complete digital documentation. An acrochordon prevention regimen was provided and long-term visits planned to monitor long term results. Further follow up revealed no return of acrochordons with no scarring or pigmentation anomalies.

Case History Number 2

A fifty seven year old male presented with a variety of the seven types of acrochordons belonging most to the pedunculated types with a few of the sessile variety. He had recently married a substantially younger woman and she had displayed disgust of the afflictee's arcochordons on several occasions, prompting the acrochordon carrier to seek alleviation treatment. The medical history revealed a high carbohydrate consumption which may have been a contributing factor to acrochordon genesis. Examination revealed twenty three acrochordons 2 to 4 millimeters in length and 2 to 3 millimeters in diameter around the neck. The axillae contained approximately a dozen acrochordons on each side which ranged in size from 4 to 7 millimeters in length and 2 to 4 millimeters in diameter. The acrochordons in the axillae were extremely firm and protuberant with a light pink coloration. Some of the acrochordons in the axillae exhibited a thicker peduncle than is usually seen, necessitating more than usual applications with a concentration of 45 percent hydrogen peroxide.

Case History Number 3

Although only one acrochordon was possessed by the twenty eight year old subject, it was located directly under the bra strap beneath the left breast and caused considerable discomfort and irritation over an extended period of time. The less than affluent means of the afflictee balked at the ninety dollar doctor quote for removal by her medical practitioner. Two simple applications of the 35 percent hydrogen peroxide acrochordon alleviation solution for Type II acrochordons were sufficient to provide complete elimination of the offending acrochordon. Follow up at three months showed no indication of re-growth and no scarring.

ACROCHORDON ALLEVIATION STUDY RESULTS

Twenty-one persons afflicted with acrochordons were treated with the present invention. Two persons did not complete the treatment program due to other obligations. The nineteen persons who continued treatment all showed improvement evidenced by complete removal of some or all of their acrochordons after one to five treatments with the present invention. In most instances, it was almost impossible to tell where the acrochordon had been after it depedunculated. On a few subjects, especially those with darkly pigmented acrochordons and fair skin, a small dot remained after acrochordon depedunculation that appears to be fading over time. The procedure was well tolerated by all subjects except two who displayed unusual sensitivity and requested premature application of the neutralizing composition. Most of the acrochordons carriers treated have shown no sign of acrochordon re-growth. One carrier continues to sprout new acrochordons but is willing to continue treatment and has stated he would not do so using a surgical removal method instead of the topical application of the present invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Type 1 Acrochordon Removal

The following is a general procedure or method for application of the selected agents and compositions for the removal of slender, stalk-like Type 1 acrochordons:

a. complete medical history form and discuss procedure with the acrochordon afflicted individual b. measure and record skin pH c. conduct full body examination to locate any various acrochordons overlooked by afflicted person and detect any just-forming acrochordons d. photograph acrochordons with 1×, 30× and 50× magnification e. degrease acrochordons with acetone f. apply neutralizer composition to skin surrounding acrochordon g. apply depedunculation composition consisting of 42 percent hydrogen peroxide
h. accelerate drying with miniature heated forced air dryer
i. watch for appearance of blanching
j. make second application of depedunculation composition if necessary
k. photograph acrochordons with 1×, 30× and 50× magnification
l. supply acrochordon afflicted person with Physician's Choice pHaze 17 rebalance cream for application eight hours post depedunculation treatment
m. inform carrier that acrochordons should spontaneously depedunculate 3 to 6 days after procedure
n. re-apply Physician's Choice pHaze 17 rebalance cream to acrochordon skin attachment site after acrochordons depedunculate
o. have patient check at weekly intervals to insure re-growth does not occur

EXAMPLE 2

Fibrofolliculoma Treatment

The following is a general method for the alleviation of the dome-shaped papules known as fibrofolliculomas and trichodiscomas which usually involve the head, neck, chest, back and arms and are frequently associated with acrochordons:

a. complete medical history form and discuss procedure with the fibrofolliculoma and trichodiscoma afflicted individual
b. measure and record skin pH
c. conduct full body examination to locate all fibrofolliculomas and trichodiscomas
d. photograph fibrofolliculomas and trichodiscomas with 1×, 30× and 50× magnification
e. cleanse fibrofolliculomas and trichodiscomas with pHaze 1 cleansing composition
f. apply pHaze 17 neutralizer crème to skin surrounding fibrofolliculomas and trichodiscomas
g. apply fibrofolliculoma and trichodiscoma apoptotic induction formulation consisting of 43 percent hydrogen peroxide
h. accelerate evaporation with miniature heated forced air dryer
i. watch for appearance of blanching
j. make second application of fibrofolliculoma and trichodiscoma apoptotic induction formulation if necessary
k. photograph fibrofolliculomas and trichodiscomas with 1×, 30× and 50× magnification
l. supply fibrofolliculoma and trichodiscoma afflicted individual with pHaze 17 rebalance cream for application eight hours post apoptotic induction treatment
m. inform fibrofolliculoma and trichodiscoma afflicted individual that apoptotic crust should form after one day and crust should separate after approximately 3 days
n. re-apply pHaze 17 rebalance cream to fibrofolliculoma and trichodiscoma lesions after crust separation
o. re-treat fibrofolliculomas and trichodiscomas two days after crust separation until complete elimination of lesions

EXAMPLE 3

Type III Acrochordon Depedunculation

Type III fat filled acrochordons known as dermatolipoma acrochordons require a modified procedure and a specialized depedunculation formulation such as the following:

a. complete medical history form and discuss procedure with the dermatolipoma acrochordon afflicted individual
b. measure and record skin pH
c. conduct full body examination to locate all Type III acrochordons
d. perform digital documentation at specified magnifications
e. dehydrate dermatolipoma surface with heated air blower after de-greasing with acetone
f. apply 35 percent hydrogen peroxide
g. re-apply 35 percent hydrogen peroxide if required for proper blanching
h. allow 3 to 5 days for dermatolipoma detachment Since special individual acrochordon and conditions may warrant changes and modifications of the present acrochordon removal and prevention invention and can be made readily by those skilled in the art of acrochordon removal and prevention without departing from the basic concept of the present invention, the present invention for acrochordon removal and prevention shall not be limited except by the scope of the appended claims.

All of the treatments and/or methods disclosed and claimed herein can be made and executed without undue experimentation in light of the present disclosure. While the treatments and methods of this invention have been described in terms of preferred embodiments, it will be apparent to those of skill in the art that variations may be applied to the treatments and/or methods and in the steps or in the sequence of steps of the method described herein without departing from the concept, spirit and scope of the invention. More specifically, it will be apparent that certain acrochordon removal and prevention agents which are both chemically and physiologically related may be substituted for the agents described herein while the same or similar results would be achieved. All such similar substitutes and modifications apparent to those skilled in the art of acrochordon removal and prevention are deemed to be within the spirit, scope and concept of the invention as defined by the appended claims.

REFERENCES

The following references, to the extent that they provide exemplary procedural or other details supplementary to those set forth herein, are specifically incorporated herein by reference:

U.S. Patents

U.S. Pat. No. 3,954,974, May 1976 to Herzog
U.S. Pat. No. 4,438,102, March 1984 to Ganci
U.S. Pat. No. 4,485,091, November 1984 to Fitton
U.S. Pat. No. 4,826,681, May 1989 to Jacquet, et al.
U.S. Pat. No. 5,380,764, January 1995 to Herzog
U.S. Pat. No. 5,376,582, April 1998 to Devillez
U.S. Pat. No. 5,958,984, September 1999 to Devillez Other Publications Books Fitzpatrick, Thomas B.; Eisen, Arthur Z.; Wolff Klaus; Freedurg, Irwin M.; and Austen, K. Frank, editors. In: *Dermatology in General Medicine*, $3^{th}$ edition, New York: McGraw-Hill, page 1036; 1991.

Graham-Brown, R.; Burns, T.: Benign and Malignant Skin Tumors. In: *Lecture Notes on Dermatology* $7^{th}$ edition, Oxford UK: Blackwell Science Ltd., pages 121–123; 1996.

King, L. E.; Stoscheck, C. M.; Gates, R.; and Nanney, L. B.: Epidermal growth factor and related growth factors. In:

Goldsmith, Lowell A. editor. *Biochemistry and Physiology of the Skin*. New York: Oxford University Press, pages 329–350; 1991.

Lever, Walter F.: Tumors of Fibrous Tissue. In: *Histopathology of the Skin*, 7th edition, Philadelphia: Lippincott, pages 664–665; 1947.

Macleod, J. M. H.: *Practical Handbook of the Pathology of the Skin*. London: H. K. Lewis, 91, 132; 1903.

Pinkus, H.; Mehregan, A. H.: In: *A Guide to Dermatohistopathology* 3rd edition, New York: Appleton Century Crofts, page 481; 1981.

Sanderson K. V.; and MacKie, R.: Epidermal Skin Tumors: In: Rook, J. N.; Wilkinson, S. A.; and Ebling, T. M., editors. *Textbook of Dermatology* 5th edition. Oxford: Blackwell, page 1468; 1992.

Sutton, R. L.; and Sutton, R. L. Jr.: *Handbook of Diseases of the Skin*. St. Louis: C. V. Moseby Company, 589; 1949.

Wilson, E.: Developmental and Nutritive Affections. In: *Diseases of the Skin* 7th edition, Philadelphia, 328–329; 1868.

Journal Articles

Agarwal, Jugal K.; and Nigam, Pramod K.: Acrochordon: A Cutaneous Sign of Carbohydrate Intolerance. *Australasian Journal of Dermatology* 28(3): 132–133; 1987.

Banik, R.; and Lubach, D.: Skin Tags: Localization and Frequencies According to Sex and Age. *Dermatologica* 174(4): 180–183; 1987.

Becker, S. W.: Benign Epidermal Neoplasms. *Archives of Dermatology and* 26: 838- ; 1932.

Beitler, Martin; Eng, Angie; Kilgour, Marta; and Lebwohl, Mark: Association Between Acrochordons and Colonic Polyps. *Journal of the American Academy of Dermatology* 14(6): 1042–1044; 1986.

Bilotta, Jeffrey; and Waye, Jerome D.: Hydrogen Peroxide Enteritis: the "Snow White" Sign. *Gastrointestinal Endoscopy* 35: 428–430; 1989.

Birt, Arthur R.; Hogg, Georgina R.; and Dube, W. James: Hereditary Multiple Fibrofolliculomas with Trichodiscomas and Acrochordons. *Archives of Dermatology* 113(12): 1674–1677; 1977.

Brendler, Sarah J.; Watson, Randy D.; Katon, Ronald M.; Parson, Mark E.; and Howatt, Janis L.: Skin Tags are not a Risk Factor for Colorectal Polyps. *Journal of Clinical Gastroenterology* 11(3): 299–302; 1989.

Brickner, Samuel M.: Fibroma Molluscum Gravidarum. *American Journal of Dermatology and Genito-Urinary Disease* 16: 240–243; 1912.

Brickner, S. M.: Fibroma Molluscum Gravidarum: A New Clinical Entity. *American Journal of Obstetrics and Gynecology* 53: 191–199; 1906.

Christensen, David W.; Faught, William E.; Black, Richard E.; Woodward, George A.; and Timmons, Otwell D.: Fatal Oxygen Embolization after Hydrogen Peroxide Ingestion. *Critical Care Medicine* 20(4): 543–544; 1992.

Danis, Richard K.; and Brodeur, Armand E.: The Danger of Hydrogen Peroxide as a Colonic Irrigating Solution. *Journal of Pediatric Surgery* 2(2): 131–133; 1967.

Dianzani, C.; Calvieri S.; Pierangeli A.; Imperi M.; Bucci M.; and Degener A. M.: The Detection of Human Papillomavirus DNA in Skin Tags. *British Journal of Dermatology* 138(4): 649–651; 1998.

Dickson, Kurt F.; and Caravati, E. Martin: Hydrogen Peroxide Exposure—325 Exposures Reported to a Regional Poison Control Center. *Clinical Toxicology* 32(6): 705–714; 1994.

Errickson, Carla V.; and Matus, Nancy R.: Skin Disorders of Pregnancy. *American Family Physician* 49(3): 610; 1994.

Giberson, Thomas P.; Kern, Joseph D.; Pettigrew, D. W. III; Eaves, Charles C.; and Haynes, John F. Jr.: Near-Fatal Hydrogen Peroxide Ingestion. *Annals of Emergency Medicine* 18(7): 778–779; 1989.

Gniadecka, Monika; Wulf, Hans C.; Nielsen, Ole F.; Christensen, Daniel H.; and Hercogova, Jana: Distinctive Molecular Abnormalities in Benign and Malignant Skin Lesions: Studies by Raman Spectroscopy. *Photochemistry and Photobiology* 66(4): 418–423; 1997.

Goette, Detlef K.; Odom, Richard B.: Skin Blanching Induced by Hydrogen Peroxide. *Southern Medical Journal* 70(5): 620–622; 1977.

Gruber, Ronald P.; Vistnes, Lars; and Pardoe, Russel: The Effect of Commonly Used Antiseptics on Wound Healing. *Plastic and Reconstructive Surgery* 55(4): 476; 1975.

Henry, Mark C.; Wheeler, Jeffrey; Mofenson, Howard C.; Caraccio, Thomas R.; Marsh, Marylin; Comer, Gail M.; and Singer, Adam J.: Hydrogen Peroxide 3% Exposures. *Clinical Toxicology* 34(3): 323–327; 1996.

Humberston, C. Lynn; Dean, Bonnie S.; and Krenzelok, Edward P.: Ingestion of 35% Hydrogen Peroxide. *Clinical Toxicology* 28(1): 95–100; 1990.

Klein-Szanto, A. J. P.; and Slaga, T. J.: Effects of Peroxides on Rodent Skin: Epidermal Hyperplasia and Tumor Promotion. *The Journal of Investigative Dermatology* 79: 30–34; 1982.

Mathur, S. K.; and Bhargava, P.: Insulin Resistance and Skin Tags. *Dermatology* 195(2): 184; 1997.

Morgolis, J.; Morgolis, L. S.: Skin Tags—A Frequent Sign of Diabetes Mellitus. *New England Journal of Medicine* 294: 1184; 1976.

Nanney, Lillian B.; Ellis, Darrell L.; Levine, Jeff; and King, Lloyd E.: Epidermal Growth Factor Receptors in Idiopathic and Virally Induced Skin Diseases. *American Journal of Pathology* 140(4): 915–925; 1992.

Nanney, Lillian B.; Gates, Ronald E.; Todderud, Gordon; King, Lloyd E. Jr.; and Carpenter, Graham: Altered Distribution of Phospholipase C-$\gamma$1 in Benign Hyperproliferative Epidermal Diseases. *Cell Growth and Differentiation* 3(4): 233–239; 1992.

Norris, P. G.; Mc Fadden, J.; Gale, E.; and Griffiths, W. A.: Skin Tags are More Closely Related to Fasting Insulin Than Fasting Glucose Levels. *Acta-Dermato Venereologica* 68(4): 367–368; 1988.

Oliver, T. H.; and Murphy, D. V.: Influenzal Pneumonia: The Intravenous Injection of Hydrogen Peroxide. *The Lancet*: 432–433; 1920.

O'Toole, Edel A.; Goel, Mimi; and Woodley, David T.: Hydrogen Peroxide Inhibits Human Keratinocyte Migration. *Dermatologic Surgery* 22: 525–529; 1996.

Pennys, Neal S.: Skin Tags do not Contain Cutaneous Nerves. *Archives of Dermatology* 126(12): 1654–1655; 1990.

Potter, Thomas S.; Sharata, Harry H.; Su, W. P. Daniel; and Hashimoto, Ken: Pedunculated Proliferative Papillomatosis. *Cutis* 57(6): 451–452; 1996.

Pujol, R. M.; Llistosella, E.; Taberner, R.; Matias-Guiu X.; Alomar A.: Acrochordons in Birt-Hogg-Dube Syndome, Histopathological Study. *American Journal of Dermatopathology* 20: 587; 1998.

Pumphrey, R. E.: Hydrogen Peroxide Proctitis. *American Journal of Surgery* 81: 60–68; 1951.

Rathbun, Edwin D.: A Method for Removing the Acrochordon (Skin Tag). *Kansas Medicine* 91(1): 11–12; 1990.

Sebben, Jack E.: Contamination Risks Associated with Electrosurgery. *Archives of Dermatology* 126(6): 805–808; 1990.

Sebben, Jack E.: Fire Hazards and Electrosurgery. *Journal of Dermatologic Surgery and Oncology* 16(5): 421–424; 1990.

Sebben, Jack E.: The Hazards of Electrosurgery. *Journal of the American Academy of Dermatology* 16(4): 869–872; 1987.

Segal, Alan; Liquid Nitrogen Therapy. *Australian Family Physician* 13(5): 356–357; 1984.

Snow, Stephen N.; Stiff, Mark A.; and Lambert, David R.: Scapel Sculpturing Techniques and Dermatologic Surgery. *Journal of Dermatologic Surgery and Oncology* 20(2): 120–126; 1994.

Spiller, William F.; and Spiller, Rachel F.: Cryoanesthesia and Electrosurgical Treatment of Benign Skin Tumors. *Cutis* 35(6): 551–552; 1985.

Strohmer, Heinz; Öztürk, Dilek; and Egarter, Christian: Use of Hydrogen Peroxide for Vaginal Contraception. *Human Reproduction* 12(7): 1599–1604; 1997.

Strother, Germaine D.: Acrochordonectomy Made Easy. *Clinician Reviews* 8(3): 154–155; 1998.

Taylor, R. W.: On the Mode of Development and Course of Molluscum Fibrosum and on the Question of Its Relationship to Acrochordon and Other Cutaneous Outshoots. *Journal of Cutaneous and Genito-Urinary Disease* 5: 41–51; (Feb.) 1887.

Tegner, Eva: Induction of Skin Blanching by Hydrogen Peroxide. *Acta Dermatologica Venereologica (Stockholm)* 74: 474–475; 1994.

Tegner, Eva; and Björnberg, Alf: Hydrogen Peroxide Cream for the Prevention of White Pressure Areas in UVA Sunbeds. *Acta Dermatologica Venereologica (Stockholm)* 70: 75–76; 1990.

Templeton, H. J.: Cutaneous Tags of the Neck. *Archives of Dermatology and Syphilology* 33: 495–505; 1936.

Tomkins, Robert R.: Skin Tags and Diabetes. *Archives of Dermatology* 113(10): 1463; 1977.

Tur, Ethel; Bolton, Laura; and Constantine, Barry E.: Topical Hydrogen Peroxide Treatment of Ischemic Ulcers in the Guinea Pig: Blood Recruitment in Multiple Skin Sites. *Journal of the American Academy of Dermatology* 33: 217–221; 1995.

Waisman, Morris: Cutaneous Papillomas of the Neck. *Southern Medical Journal* 50: 725–732; 1957.

Weigand, Dennis A.: Microscopic Features of Lichen Sclerosus et Atrophicus in Acrochordons: A Clue to the Cause of Lichen Sclerosus et Atrophicus? *Journal of the American Academy of Dermatology* 28(5 pt 1): 751–754; 1993.

Wilson, E.: The Dermal Pathology of Hippocrates. *Journal of Cutaneous Medicine* 2: 17- ; 1868.

Wilson, E.: The Dermal Pathology of Paulus AEgineta.

Wilson, E: The Dermal Pathology of Celsus. *Appendix to Journal of Cutaneous Medicine* 2: 12- ;186?.

Zuber, Thomas J.: The Price Tag for Skin Tags. *Hospital Practice (Office Edition)* 32(3): 221–222; 1997.

What is claimed is:

1. A method for the removal of acrochordons comprising:
   (a) obtaining a composition comprising hydrogen peroxide in a concentration of at least 23 percent; and
   (b) applying said composition to an acrochordon on an acrochordon afflicted person or domesticated animal.

2. The method of claim 1, wherein the concentration of hydrogen peroxide is from about 23 percent to about 60 percent.

3. The method of claim 1, wherein the concentration of hydrogen peroxide is from about 35 percent to about 60 percent.

4. The method of claim 3, wherein the concentration of hydrogen peroxide is from about 35 percent to about 40 percent.

5. The method of claim 3, wherein the concentration of hydrogen peroxide is from about 40 percent to about 50 percent.

6. The method of claim 5, wherein the concentration of hydrogen peroxide is from about 43 percent to about 48 percent.

7. The method of claim 1, wherein the composition further comprises at least one vitamin.

8. The claim 7, wherein the vitamin is selected from the group consisting of ascorbic acid, niacin, thiamin and riboflavin.

9. The method of claim 8, wherein the vitamin is L-ascorbic acid.

10. The method of claim 1, wherein the composition further comprises at least one amino acid.

11. The method of claim 10, wherein the amino acid is selected from the group consisting of tyrosine, phenylalanine, carnitine, arginine, glycine, alanine, valine, leucine, isoleucine, serine, threonine, cysteine, cystine, methionine, asparagine, glutamine, lysine, 5-hydroxylysine, histidine, tryptophan, proline, ornithine and carnosine.

12. The method of claim 11, wherein the amino acid is L-carnitine.

13. The method of claim 1, wherein the composition further comprises at least one melanin inhibitor.

14. The method of claim 13, wherein the melanin inhibitor is selected from the group consisting of hydroquinone, niacinimide, cinnamic acid, gamma-L-glutamyl-L-cystine, gamma-L-cysteine, oxidized glutathione, phenol, polyphenol, linoleic acid, ellagic acid, glycyrrhizic acid, alkylsalicylic acid, kojic acid, kojic acid glycosides, kojic acid succinimide ester, kojic acid dimer, thiazoles, propionic acid, sulphur, kudzu root, lavanol, caffeic acid, dicaffeoylquinic acid, tricaffeoylquinic acid, vitamin K, hydantoin, tranexamic acid, chromone derivative, indomethicin methacin, erthorbic acid, glucoside, conchiolin hydrolyzate, licorice root extract, logwood extract, gromwell seed extract, arbutin, chitosan, superoxide dismutase, melanostatin, S-lactoyl glutathione, and hydroquinone glycoside.

15. The method of claim 14, wherein the melanin inhibitor is kojic acid.

16. The method of claim 1, wherein the composition further comprises at least one organic acid.

17. The method of claim 16, wherein the organic acid is selected from the group consisting of lactic acid, citric acid, isocitric acid, glycolic acid, malic acid, tartronic acid, tartaric acid, glucoronic acid, pyruvic acid, acetyl pyruvic acid, β-fluoropyruvic acid, 2-hydroxy isobutyric acid, galacturonic acid, salicylic acid, succinic acid, mandelic acid, β-phenyllactic acid, saccharic acid, β-phenylpyruvic acid, α-hydroxybutyric acid, α-hydroxyisobutyric acid, mucic acid, atrolactic acid, glucoheptonic acid, gluconic acid, glyceric acid, quinic acid, glyceruric acid, threuric acid, erythreuric acid, xyluric acid, lyxuric acid, arabinuric acid, riburic acid, iduric acid, guluric acid, mannuric acid, altruric acid, alluric acid, taluric acid, xylaric acid, lyxaric acid, trihydroxybutanoic acid, pentahydroxyhexanoic acid and hexahydroxyheptanoic acid.

18. The method of claim 17, wherein the organic acid is L-lactic acid.

19. The method of claim 1, wherein the composition further comprises at least one hormone.

20. The method of claim 19, wherein the hormone is selected from the group consisting of dehydroepiandrosterone, progesterone, estrogen, melatonin, testosterone, pregnenolone, thyroid hormone, thymus hormone and human growth hormone.

21. The method of claim 1, wherein the composition further comprises at least one sulfoxide.

22. The method of claim 21, wherein the sulfoxide is selected from the group consisting of dimethylsulfoxide and decylmethylsulfoxide.

23. The method of claim 22, wherein the sulfoxide is dimethylsulfoxide.

24. The method of claim 1, wherein the composition further comprises at least one alcohol.

25. The method of claim 24, wherein the alcohol is selected from the group consisting of ethanol, propanol, butanol, pentanol, hexanol, octanol, nonanol, decanol, 2-butanol, 2-pentanol and benzyl alcohol.

26. The method of claim 25, wherein the alcohol is ethanol.

27. The method of claim 1, wherein the composition comprises at least one fatty acid.

28. The method of claim 27, wherein the fatty acid is selected from the group consisting of valeric acid, heptanoic acid, pelagonic acid, caproic acid, capric acid, lauric acid, myristic acid, stearic acid, oleic acid and caprylic acid.

29. The method of claim 28, wherein the fatty acid is myristic acid.

30. The method of claim 1, wherein the composition further comprises at least one fatty acid ester.

31. The method of claim 30, wherein the fatty acid ester is selected from the group consisting of isopropyl myristate, isopropyl palmitate, octyldodecyl myristate, ethyl acetate, butyl acetate, methyl acetate, methylvalerate, methylpropionate, diethyl sebacate and ethyl oleate.

32. The method of claim 31, wherein said fatty acid ester is isopropyl palmitate.

33. The method of claim 1, wherein the applying step is by brush, dropper, atomizer, injector, sprayer or pipette.

34. The method of claim 1, wherein the composition further comprises at least one polyol.

35. The method of claim 34, wherein the polyol may be selected from the group consisting of propylene glycol, polyethylene glycol, ethylene glycol, diethylene glycol, triethylene glycol, dipropylene glycol and glycerol.

36. The method of claim 35, wherein the polyol is propylene glycol.

37. The method of claim 1, wherein the composition further comprises at least one amide.

38. The method of claim 37, wherein the amide may be selected from the group consisting of urea, dimethylacetamide, diethyltoluamide, dimethylformamide, dimethyloctamide, dimethyldecamide, hexamethylenelauramide, diethanolamine and triethanolamine.

39. The method of claim 38, wherein the amide is dimethylformamide.

40. The method of claim 1, wherein the composition further comprises at least one surfactant.

41. The method of claim 40, wherein the surfactant may be selected from the group consisting of sodium laurate, sodium lauryl sulphate, cetyltrimethyl ammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride, Poloxamer (231, 182, 184), Brij (30, 93, 96,99), Span (20, 40, 60, 80), Myrj (45, 51, 52), Miglyol 840, sodium cholate, sodium salts of taurocholic, glycholic, desoxycholic acids and lecithin.

42. The method of claim 41, wherein the surfactant is lecithin.

43. The method of claim 1, wherein the composition further comprises at least one terpene.

44. The method of claim 43, wherein the terpene may be selected from the group consisting of D-limonene, α-pinene, β-carene, α-terpineol, terpinen-4-ol, carvol, carvone, pulegone, piperitone, menthone, cyclohexene oxide, limonene oxide, α-pinene oxide, cyclopentene oxide, 1,8-cineole, ylang ylang, anise, chenopodium and eucalyptus.

45. The method of claim 44, wherein the terpene is clyclohexene oxide.

46. The method of claim 1, wherein the composition further comprises at least one alkanone.

47. The method of claim 46, wherein the alkanone may be selected from the group consisting of N-heptane, N-octane, N-nonane, N-decane, N-undecane, N-dodecane, N-tridecane, N-tetradecane and N-hexadecane.

48. The method of claim 47, wherein the alkanone is N-octane.

49. The method of claim 1, wherein the composition further comprises aloe vera.

50. The method of claim 1, wherein the composition further comprises at least one gamma linolenic precursor.

51. The method of claim 50, wherein the gamma linolenic acid precursor may be selected from the group consisting of borage oil, black currant oil and evening primrose oil.

52. A method for the removal of acrochordons comprising:
(a) obtaining a composition comprising hydrogen peroxide in a concentration of at least 23 percent and at least one compound selected from a vitamin, an amino acid, a melanin inhibitor, an organic acid, a hormone, a sulfoxide, an alcohol, a fatty acid, a fatty acid ester, a polyol, an amide, a surfactant, a terpene, an alkanone, aloe vera and a gamma linolenic precursor; and
(b) applying said composition to an acrochordon on an acrochordon afflicted person or domesticated animal.

53. The method of claim 52, wherein the concentration of hydrogen peroxide is from about 23 percent to about 60 percent.

54. The method of claim 52, wherein the concentration of hydrogen peroxide is from about 35 percent to about 60 percent.

55. The method of claim 52, wherein the concentration of hydrogen peroxide is from about 35 percent to about 40 percent.

56. The method of claim 52, wherein the concentration of hydrogen peroxide is from about 40 percent to about 50 percent.

57. The method of claim 52, wherein the concentration of hydrogen peroxide is from about 43 percent to about 48 percent.

58. The method of claim 52, wherein the composition comprises kojic acid, dimethylsulfoxide, melatonin, L-ascobic acid and ethanol.

59. The method of claim 58, wherein the composition comprises 26 percent hydrogen peroxide, 2 percent kojic acid, 12 percent dimethylsulfoxide, 0.5 percent melatonin, 1 percent L-ascobic acid and 15 percent ethanol.

60. The method of claim 52, wherein the composition comprises hydrogen peroxide, lactic acid, niacin, testosterone, licorice root extract and β-phenylpyruvic acid.

61. The method of claim 60, wherein the composition comprises 47 percent hydrogen peroxide, 14 percent lactic acid, 2 percent niacin, 2 percent testosterone, 1 percent licorice root extract and 0.5 percent β-phenylpyruvic acid.

62. The method of claim 52, wherein the composition comprises L-tyrosine, phenylalanine, tricaffeoylquinic acid and ethanol.

63. The method of claim 62, wherein the composition comprises 23 percent hydrogen peroxide, 2 percent L-tyrosine, 2 percent phenylalanine, 1 percent tricaffeoylquinic acid and 18 percent ethanol.

64. The method of claim 52, wherein the composition comprises hydrogen peroxide, lactic acid, glycolic acid, salicylic acid, citric acid and ethanol.

65. The method of claim 64, wherein the composition comprises 23 percent hydrogen peroxide, 4 percent lactic acid, 4 percent glycolic acid, 4 percent salicylic acid, 4 percent citric acid and 20 percent ethanol.

66. The method of claim 52, wherein the composition comprises dimethysulfoxide.

67. The method of claim 66, wherein the composition comprises 35 percent hydrogen peroxide and 35 percent dimethysulfoxide.

68. The method of claim 52, wherein the composition comprises L-ascorbic acid, niacin, glycine, hydroquinone, superoxide dismutase, galacturonic acid and ethanol.

69. The method of claim 68, wherein the composition comprises 35 percent hydrogen peroxide, 0.5 percent L-ascorbic acid, 0.5 percent niacin, 0.5 percent glycine, 0.5 percent hydroquinone, 0.5 percent superoxide dismutase, 5 percent galacturonic acid and 14 percent ethanol.

70. The method of claim 52, wherein the composition comprises decylmethylsulfoxide.

71. The method of claim 59, wherein the composition comprises 60 percent hydrogen peroxide and 6 percent decylmethylsulfoxide.

* * * * *